United States Patent [19]

Yu et al.

[11] Patent Number: 5,939,395
[45] Date of Patent: Aug. 17, 1999

[54] IDENTIFICATION OF A POTENT ANTIOXIDANT FROM *ALOE BARBADENSIS*

[75] Inventors: Byung Pal Yu, San Antonio, Tex.; Ki-Young Lee, Cheonansi, Rep. of Korea

[73] Assignee: Board of Regents, The University of Texas System, Austin, Tex.

[21] Appl. No.: 08/973,059

[22] PCT Filed: Jun. 7, 1995

[86] PCT No.: PCT/US95/07404

§ 371 Date: Sep. 18, 1998

§ 102(e) Date: Sep. 18, 1998

[87] PCT Pub. No.: WO96/40182

PCT Pub. Date: Dec. 19, 1996

[51] Int. Cl.⁶ .......................... A61K 35/78; A61K 31/70

[52] U.S. Cl. ............................................. 514/23; 424/195.1

[58] Field of Search ............................. 424/195.1; 514/23

[56] References Cited

U.S. PATENT DOCUMENTS

| 4,656,029 | 4/1987 | Grollier et al. | 424/47 |
| 5,308,838 | 5/1994 | McAnalley et al. | 514/54 |
| 5,420,114 | 5/1995 | Clodman et al. | 514/23 |

*Primary Examiner*—Raymond Henley, III
*Attorney, Agent, or Firm*—Swanson & Bratschun LLC

[57] ABSTRACT

The present invention is directed to a method for providing an antioxidant compound to a patient in need thereof which comprises the administration of a phenolic compound isolated from *Aloe barbadensis* and to methods for isolating the phenolic compound.

4 Claims, 2 Drawing Sheets

IDENTIFICATION OF A POTENT ANTIOXIDANT FROM *ALOE BARBADENSIS*

This application is a 371 of PCT/US95/07404 filed Jun. 7, 1995.

FIELD OF THE INVENTION

The present invention relates to the field antioxidants. Specifically, it relates to the identification and purification of a phenolic compound isolated from *Aloe barbadensis*, which is shown to exhibit potent antioxidant activity.

BACKGROUND OF THE INVENTION

The Aloe plant is an intricate plant which contains many biologically active substances. (Cohen et al. in *Wound Healing/Biochemical and Clinical Aspects*, 1st ed. W B Saunders, Philadelphia (1992)) Studies have shown that the majority of these biologically active substances are located in a clear gel fillet located in the center of Aloe leaves. Historically, Aloe products have been used in dermatological applications for the treatment of burns, sores and other wounds. These uses have stimulated a great deal of research on identifying compounds from Aloe plants that have clinical activity, especially anti-inflammatory activity. (See, e.g., Grindlay and Reynolds (1986) J. of Ethnopharmacology 16:117–151; Hart et al. (1988) J. of Ethnopharmacology 23:61–71) As a result of these studies there have been numerous reports of Aloe compounds having anti-tumor, anti-gastric ulcer, anti-diabetic and anti-tyrosinase activity. (See, e.g. Yag et al. (1977) Z. Naturforsch 32c:731–734).

The anti-inflammatory activity of Aloe compounds has been extensively investigated. Studies by Davis et al. have shown that Aloe not only reduces inflammation, but also improves wound healing. (Davis et al. (1994) J. Am. Podiatric Med. Assoc. 84:77–81, Davis et al. (1989) J. Am. Podiatric Med. Assoc. 79:395–397). The anti-inflammatory/wound healing ability of Aloe has been attributed to a growth factor-like substance that activates the wound healing and inflammation reduction processes. (Davis et al. (1994) J. Am. Podiatric Med. Assoc. 84:77–81, Davis et al (1989) J. Am. Podiatric Med. Assoc. 79:395–397).

Despite the great deal of activity that has taken place in this area, to date, there have been no reports on the possible presence of antioxidants in Aloe plants and their physiological effects in biological systems. Naturally occurring antioxidants are primarily polyphenolic compounds, many of which are found in plants. Phenolic antioxidants have been found to function as free radical terminators and metal chelators. They are primarily used as food additives and nutritional supplements. A great deal of research has been conducted to identify naturally occurring phenolic antioxidants. Examples of some common plant phenolic antioxidants include flavonoid compounds, cinnamic acid derivatives, coumarins, tocopherols, and polyfunctional organic acids. Some of these compounds, including flavanols, Schisanbanol and Schizandrin B, are now commercially available. See, e.g., Bors and Saran (1987) Free Rad. Res. Comms. 2:289–295, Robak and Gryglewski (1988) Biochem. Pharmacol. 37:837–841, Das and Ratty (1986) in *Plant Flavonoids in Medicine: Biochemical, Pharmacological, and Structure-Activity Relationship* (Cody, Middleton, and Harborne, (eds)) Alan R. Liss, New York, Laughton et al. (1989) Biochem. Pharmacol. 38:2859–2867, Xue et al. (1992) Free Rad. Biol. Med. 12:127–135.

SUMMARY OF THE INVENTION

The present invention describes the identification and purification of a phenolic compound, isolated from *Aloe barbadensis*, which exhibits potent antioxidant activity. The structure of this compound, referred to herein as Aloe antioxidant #556, is shown in FIG. 1. This compound was first isolated and its structure determined by Speranza and coworkers from Kenya aloe which is obtained from *Aloe ferox*. (Speranza et al. (1986) Phytochemistry 25:2219–2222.) Preliminary tests indicate that this compound is a more effective antioxidant than vitamins E or C.

This invention also includes an improved method for isolating and purifying this compound. A flow chart of the improved method of the present invention is set forth in FIG. 2.

DETAILED DESCRIPTION OF THE PREFERRED EMBODIMENTS

Figure 1:
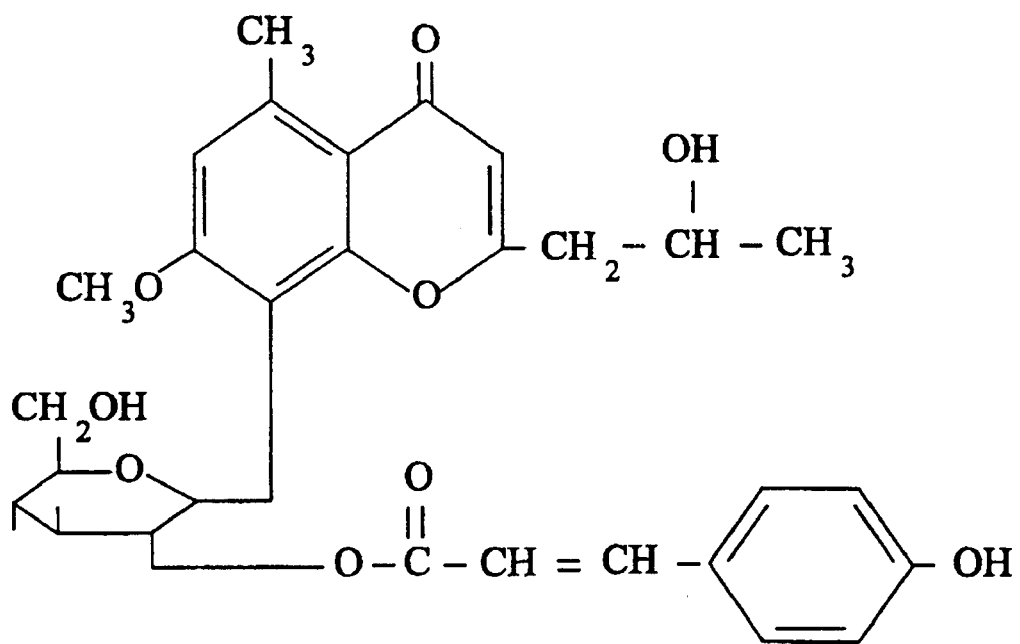
FIG. 1 illustrates the chemical structure of Aloe antioxidant #556.

The present invention describes the identification and purification of a phenolic compound, isolated from *Aloe barbadensis*, which exhibits potent antioxidant activity. The structure of this compound, which has a molecular weight of 556 g/mole, is set forth in FIG. 1. This compound, referred to herein as Aloe antioxidant #556, has greater antioxidative activity than either Vitamins C or E. This is the first report of an antioxidant isolated from Aloe.

This invention further provides an improved method for purifying this compound.

Figure 2:
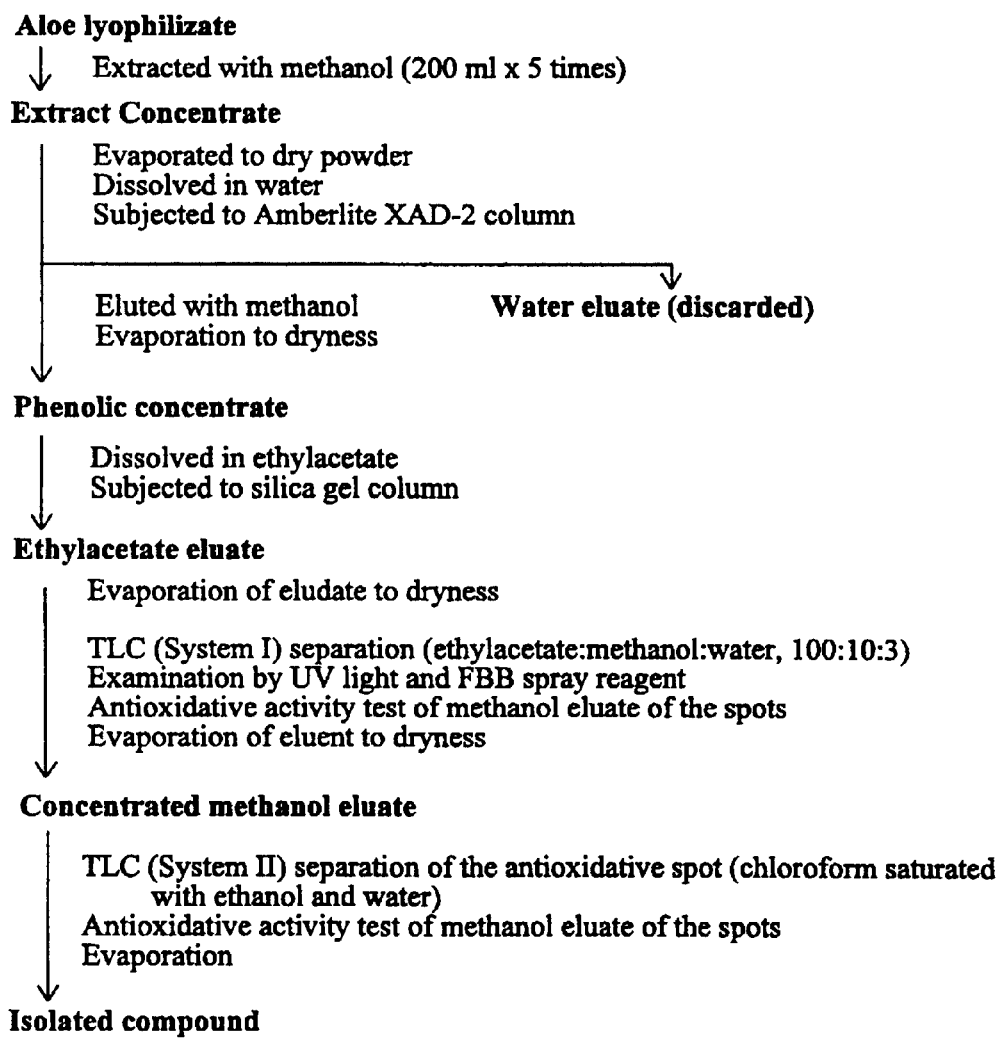
FIG. 2 depicts the method of this invention in a flowsheet format.

Example 1 describes the isolation and purification of Aloe antioxidant #556. The procedure followed is set forth in a flow diagram in FIG. 2. The separation procedure was a modification of the method of Yagi et al. (1986) Planta Med. 3:213–218. Briefly, Aloe lyophilizate was extracted with methanol and separations were performed on an Amberlite XAD-2 chromatography column to remove polar sugars, amino acids and other impurities. The partially purified lyophilizate was then dissolved in ethyl acetate and repeatedly eluted through a silica gel column with ethyl acetate. It is this step which represents a significant improvement over the prior art method of Yagi.

The method of Yagi uses a sequential fractionation procedure, with a number of mixed solvent systems of ethyl acetate, acetone and methanol. In examining a number of different eluants of increasing polarity, including ethyl acetate, ethyl acetate:acetone (4:1), ethyl acetate:acetone (3:1), acetone and methanol, it was discovered that the pure ethyl acetate fractions contained more potent antioxidants than any of the more polar fractions.

Following the silica gel chromatography described above, the concentrated mixture was further purified using two separate thin layer chromatography (TLC) systems. Several of the separated bands from the first TLC system exhibited antioxidative activity. These bands were isolated and further separated with the second TLC system. Several of the bands separated from the second TLC system also exhibited antioxidative activity. One of these bands, which exhibited appreciable antioxidative activity, was isolated and further purified again using the second TLC system.

The purified compound exhibited only one peak upon high pressure liquid chromatography (HPLC) analysis (data not shown). This compound has been identified as C-5-methyl chromone glycosylated with coumaric acid by analysis with HPLC, gas chromatograph-mass spectrometry (GS-MS), and nuclear magnetic resonance (NMR) (data not shown). The molecular weight of the compound was found to be 556.6 (thus, tentatively termed as Aloe antioxidant #556). The structure of this compound is set forth in FIG. 1.

The antioxidative activity of antioxidant #556, was evaluated by measuring the extent of the suppression of lipid peroxidation using two standard methods: the MDA (Malondialdehyde) and DCF (Dichlorofluorescein) methods. The MDA method is the most widely used and the DCF method was used to complement the MDA data. Two bioassay systems—peroxidation of rat brain homogenate and isolated rat liver microsome induced by the NADPH/ADP-$Fe^{2+}$ system for lipid peroxidation—were used for the evaluation. The rat brain homogenate system was selected because of its similarity to environments for in vivo peroxidations. The MDA method measures suppression of the production of malondialdehyde. Malondialdehyde is one of the major by-products of lipid peroxidation and thus, is commonly used as a means of measuring the extent of lipid peroxidation. The amount of malondialdehyde present is measured using barbituric acid (TBA). The DCF method measures the suppression of free radical generation. Like malondialdehyde, free radicals are also generated as a result of lipid peroxidation. The concentration of free radicals is measured using dichlorofluorescin-diacetate. The greater the inhibition of MDA and free radicals formation respectively, the more effective a compound is as an antioxidant. The results are set forth in Table 1.

As can be seen in Table 1, after incubation for 10 minutes MDA production was inhibited by 16% and free radical production was inhibited by 57% over the control sample. After 30 minutes, however, inhibition of MDA production increased 70% over the control and free radical production was inhibited by 84% over the control. These results indicate that Aloe antioxidant #556 is a potent antioxidant.

The antioxidative activity of this compound was compared to several commercial antioxidants, including tocopherol, propyl galate and BHA and also with some other phenolic Aloe components, such as, coumaric acid, feruloyl aloesin and barbaloin. These results are set forth in Table 2. The antioxidant efficacy was estimated by the % inhibition of lipid peroxidation using the MDA and DCF methods, as described above. At the concentration of 0.5 mM, the suppression of MDA production by Aloe antioxidant #556 was 98%, equivalent to the effectiveness of tocopherol at the same concentration. However, at the lower concentration of 0.1 mM, Aloe antioxidant #556 was significantly more effective than tocopherol (92% v 58%). Feruloyl aloesin showed moderate antioxidative activity, with an MDA suppression rate of 59% at a concentration of 0.5 mM, but the suppression rate was decreased to less than half at 0.1 mM. This trend was similar in the case of coumaric acid. Barbaloin showed a very weak antioxidative effect. These results indicate not only that Aloe antioxidant #556 is an effective antioxidant, but that its effective activity range may be seen at lower concentrations than other commonly used naturally-occurring antioxidants.

As a potent antioxidant, there are a number of potential uses for compound #556, including use as a food additive, such as BHA or BHT or use as a nutritional supplement, such as vitamins A and E. Aloe antioxidant #556 may also have some possible therapeutic uses. Those skilled in the art will be able to appropriately formulate compound #556 to most effectively make the compound available to the subject for the desired application. The antioxidant activity data presented herein also allows those skilled in the art to adopt the appropriate dosages for the desired application.

The present application includes the use of compound #556 as an antioxidant. Also included within the scope of this application is the use of analogs of compound #556 that are either derived from *Aloe barbadensis* or that are obtained by minor chemical alterations of compound #556.

The following examples are provided for illustrative purposes only and are not intended to limit the scope of the invention.

EXAMPLE 1

Isolation and Purification of Aloe Antioxidant #556

Materials

Lyophilizate of *Aloe barbadensis* was supplied by Aloecorp (Irving, Tex.), in both a processed and crude form. To prepare the lyophilizates, the Aloe plants were harvested with the highest degree of sanitation and the gel was filleted from the leaves of the plants. Pulps were removed from the gel by passage through 250 mesh screen and the gel was decolorized by filtering with activated charcoal and diatomaceous earth prior to the lyophilization step, which was carried out within 2 hours of filleting. Molar concentrations of the Aloe compounds were determined by the total phenolic content of the Folin-Ciocalteau reagent method. A standard curve for the method was obtained using coumaric acid (Sigma) as the standard.

Extraction of Phenolic Compounds from the Lyophilizate of *Aloe barbadensis*

As stated above, the separation procedure was a modification of the method of Yagi et al. (1986) Planta Med. 3:213–218. Briefly, 10 g of the Aloe lyophilizate was extracted five times with 200 ml of methanol. The pooled extracts were then evaporated and lyophilized to yield 0.35 g of a yellow powder. This powder was dissolved in 10 ml of distilled water and separated into individual chemical components by column chromatography utilizing styrene-divinylbenzene resin (Amberlite XAD-2, 2.5×28 cm, Mallinckrodt). Before eluting the phenolic compounds the column was first washed several times with distilled water to remove polar sugars, amino acids and other impurities from the Aloe. The phenolic compounds were then eluted with 100 ml of methanol. The methanol eluate was evaporated to dryness, yielding a yellow powder. This powder was dissolved in ethyl acetate and repeatedly eluted through a silica gel column with ethyl acetate.

Thin Layer Chromatography (TLC) and High Performance Liquid Chromatography (HPLC) Analysis The concentrated ethyl acetate fractions were further purified using thin layer chromatography (TLC) with silica gel 60 (Merck). For TLC separation, two separate isolation systems were adopted. In the first separation system, the TLC was run with a mobile phase of ethyl acetate:methanol:water (100:10:3). The plate was dried and the separated bands were examined under UV light and sprayed with 0.5% Fast Blue B reagent for coloring response. Several of the bands having Rf values between 0.40–0.55, had a coloring response of dark brown and violet. These bands were removed from the plate and the compounds were separated from the silica by eluting with methanol.

The methanol eluate concentrates were further separated with the second TLC system using chloroform sequentially saturated with ethanol and water as the mobile phase. Following development, the plate was dried and examined under UV light and sprayed with 0.5% Fast Blue B reagent. Some bands, including dark violet, blue and orange bands, showed antioxidant activity upon isolation and testing of the compounds contained in each band. Of the spots, the dark violet band was considered to be the most promising one to test, due to its appreciable amount and antioxidative activity. The silica of the TLC plate including this band was mechanically removed from the plate and eluted with methanol. The concentrated eluates were spotted again and applied to the second TLC system for further purification. Upon further purification one band showed a distinct yellow color after spraying with Fast Blue B. The purified sample showed one peak by HPLC analysis and the molecular weight of the material was determined to be 556.6 g/mole by GC-MS. The chemical structure was established by the information obtained from various chemical tests together with HPLC, GC-MS, NMR and UV scanning data (data not shown). Thus, it was possible to obtain highly purified Aloe antioxidant #556 through the application of two different sequential TLC separation systems.

EXAMPLE 2

Measurement of the Antioxidative Effect of Compound #556

MDA Method

100 μl of rat brain homogenate and approximately 10 μg of Aloe antioxidant #556 were mixed with 100 μl of 8.1% sodium dodecyl sulfate (SDS) solution in glass tubes. The mixture was centrifuged for 5 seconds, after which 1.5 ml of 20% acetic acid was added, and the mixture was centrifuged again. 1.0 ml of a 1.2% solution of thiobarbituric acid (TBA) was then added and the tubes were covered with clean marbles and put in boiling water for 30 minutes. After centrifugation at 2,000 rpm for 10 minutes, the color intensity of the supernatant was read at 532 nm by spectrophotometer (Shimadzu, UV 265).

DCF Method

150 μl of rat brain homogenate and approximately 10 μg of Aloe antioxidant #556 were added to 1.6 ml distilled water. 20 μl of 0.125 mM dichlorofluorescin-diacetate (DCFHDA) dissolved in ethanol and 10 μl of 0.1 unit esterase were added to the mixture and incubated for 10 minutes. Fluorescence intensity was measured with a spectrofluorometer (Perkin Elmer, LS 50) using an excitation wavelength at 488 nm (band width 5 nm) and emission wavelength of 525 nm (band width 20 nm). The concentration of DCF was determined by comparison to a standard DCF curve, which was constructed by plotting the fluorescence activity of samples of DCF having known concentrations. The antioxidative activity was calculated by comparison of the suppression rate of antioxidant #556 against a control using the following formula:

$$\left(1 - \frac{DCF \,(\text{or } TBA)\,\text{value of the sample}}{DCF \,(\text{or } TBA)\,\text{value of the control}}\right) \times 100\,(\%)$$

The results are set forth in Table 2.

TABLE 1

The antioxidative activity of Aloe compound #556.

| Incubation (min) | Control* | | Aloe compound | | | |
|---|---|---|---|---|---|---|
| | MDA production | Free radical production | MDA production | % inhibition | Free radical production | % inhibition |
| 10 | 9.9 | 282 | 8.3 | 16.2 | 120 | 57.4 |
| 20 | 20.4 | 698 | 8.9 | 56.4 | 148 | 78.8 |
| 30 | 29.3 | 1144 | 8.7 | 70.3 | 184 | 83.9 |

*Control samples contain no aloe #556.

TABLE 2

Comparison of Antioxidant Efficacy of #556, with other commercially available antioxidants

| | Suppression of Lipid Peroxidation (%) | | | |
|---|---|---|---|---|
| | 0.5 mM[1] | | 0.1 mM[1] | |
| Antioxidants | MDA | DCF | MDA | DCF |
| Compound #566 | 98 | 95 | 92 | 74 |
| Coumaric Acid | 57 | 34 | 20 | 0 |
| Barbaloin | 16 | 1 | 13 | 0 |
| Feruloyl aloesin | 59 | 28 | 29 | 0 |
| Tocopherol | 100 | 91 | 58 | 26 |
| Propyl galate | 100 | 95 | 97 | 77 |

[1]concentrations of the antioxidative compounds added to incubation media

We claim:

1. A method for providing an antioxidant compound to a patient in need thereof, comprised of the administration of an effective amount of an antioxidant compound derived from *Aloe barbadensis*.

2. The method of claim 1 wherein said antioxidant compound has the following structure or is an analog of:

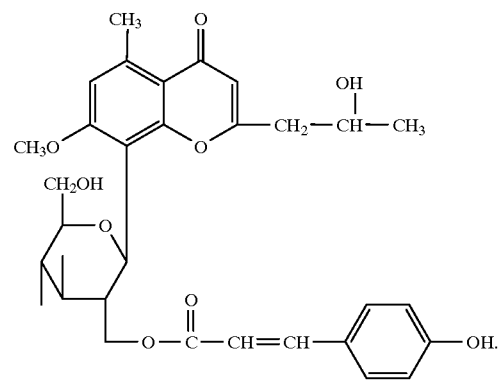

3. The method of claim 2 wherein said antioxidant compound has the structure:

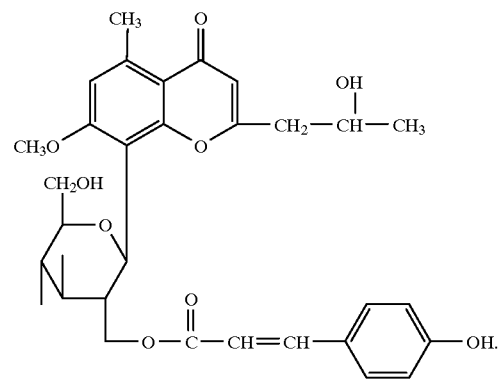

4. A method for the isolation of Aloe antioxidant compound #556 from Aloe extract, having the formula:

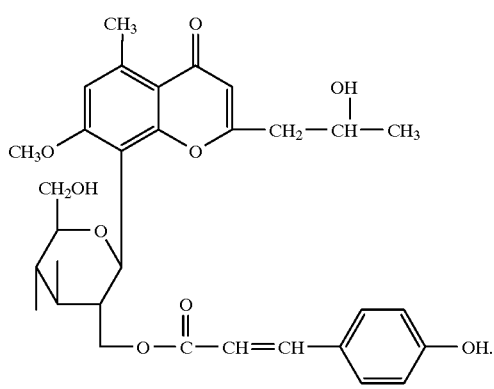

said method comprising:

a) lyophilizing an Aloe extract;

b) extracting phenolic compounds from said lyophilized extract;

c) subjecting said phenolic compounds to a first thin layer chromatography (TLC) system to isolate compounds with antioxidative activity; and d) subjecting said compounds with antioxidative activity to a second TLC system to isolate Aloe antioxidant compound 556.

* * * * *